(12) United States Patent
Hull et al.

(10) Patent No.: US 9,784,668 B2
(45) Date of Patent: Oct. 10, 2017

(54) SYSTEMS AND METHODS FOR TESTING INTERNAL BONDS

(71) Applicant: THE BOEING COMPANY, Chicago, IL (US)

(72) Inventors: John R. Hull, Seattle, WA (US); Keith John Davis, Seattle, WA (US)

(73) Assignee: The Boeing Company, Chicago, IL (US)

( * ) Notice: Subject to any disclaimer, the term of this patent is extended or adjusted under 35 U.S.C. 154(b) by 196 days.

(21) Appl. No.: 14/725,104

(22) Filed: May 29, 2015

(65) Prior Publication Data

US 2016/0349171 A1     Dec. 1, 2016

(51) Int. Cl.
*G01N 19/04*     (2006.01)
*B29C 65/82*     (2006.01)

(52) U.S. Cl.
CPC ............. *G01N 19/04* (2013.01); *B29C 65/82* (2013.01); *B29C 65/8207* (2013.01); *B29C 65/8215* (2013.01); *B29C 65/8223* (2013.01); *B29C 65/8276* (2013.01); *B29C 65/8292* (2013.01); *G01N 2203/0005* (2013.01); *G01N 2203/0016* (2013.01); *G01N 2203/0055* (2013.01); *G01N 2203/0091* (2013.01); *G01N 2203/0252* (2013.01); *G01N 2203/0658* (2013.01); *G01N 2291/0231* (2013.01); *G01N 2291/04* (2013.01);
(Continued)

(58) Field of Classification Search
CPC ............ B29C 65/8296; B29C 65/8276; B29C 65/8292; B29C 65/8215; B29C 65/8223; B29C 65/8207; B29C 65/82; G01N 2291/04; G01N 2291/042; G01N 2291/0421; G01N 2291/0422; G01N 2291/044; G01N 2291/052; G01N 2291/0231; G01N 2291/2694; G01N 2203/0658; G01N 2203/0252; G01N 2203/0091; G01N 2203/0055; G01N 2203/0016; G01N 2203/0005; G01N 19/04; G01N 29/045
USPC ..... 73/588, 827, 150 A, 627, 802, 842, 582, 73/583, 587, 620
See application file for complete search history.

(56) References Cited

U.S. PATENT DOCUMENTS 3,196,649 A * 7/1965 Furth ................. B21D 1/06
                                          29/421.1
3,453,872 A   7/1969 Botsco
(Continued)

*Primary Examiner* — Jonathan Dunlap
(74) *Attorney, Agent, or Firm* — Joseph F. Harding; The Small Patent Law Group, LLC

(57) ABSTRACT

A transducer assembly is provided. The transducer assembly includes a magnetic portion, a body, a tensile pulse transmitter, and a pulse and current control unit. The magnetic portion is configured to provide a magnetic field. The body is disposed within an opening of the magnetic portion, and has a conductive portion configured to pass electric current near a body surface oriented toward the test surface. The tensile pulse transmitter is disposed within a cavity of the body and configured to transmit a tensile pulse into the test object. The pulse and current control unit is configured to control the tensile pulse transmitted by the tensile pulse transmitter, and to provide a current that passes through the conductive portion of the body and the test object, whereby a force urging the transducer assembly and the test object toward each other is generated responsive to the magnetic field and the current.

19 Claims, 6 Drawing Sheets

(52) U.S. Cl.
CPC . *G01N 2291/042* (2013.01); *G01N 2291/044* (2013.01); *G01N 2291/0421* (2013.01); *G01N 2291/052* (2013.01); *G01N 2291/2694* (2013.01)

(56) References Cited

U.S. PATENT DOCUMENTS

| | | | |
|---|---|---|---|
| 3,576,126 A | 4/1971 | Weighart | |
| 3,703,958 A | 11/1972 | Kolm | |
| 3,825,819 A | 7/1974 | Hansen et al. | |
| 3,998,081 A * | 12/1976 | Hansen | B21D 1/06 29/419.2 |
| 4,116,031 A * | 9/1978 | Hansen | B21D 1/08 361/139 |
| 4,184,373 A | 1/1980 | Evans et al. | |
| 4,484,820 A | 11/1984 | Rosencwaig | |
| 4,538,462 A | 9/1985 | Hartog et al. | |
| 5,431,324 A | 7/1995 | Kajiwara et al. | |
| 5,624,594 A | 4/1997 | Matsen et al. | |
| 5,660,669 A | 8/1997 | Mittleider | |
| 5,833,795 A | 11/1998 | Smith et al. | |
| 5,902,935 A | 5/1999 | Georgeson et al. | |
| 6,302,314 B1 | 10/2001 | Horio et al. | |
| 6,490,047 B2 | 12/2002 | Sui | |
| 6,491,685 B2 | 12/2002 | Visuri et al. | |
| 6,613,169 B2 | 9/2003 | Georgeson et al. | |
| 6,622,568 B2 | 9/2003 | Nelson et al. | |
| 6,848,321 B2 | 2/2005 | Bossi et al. | |
| 7,017,422 B2 | 3/2006 | Heymann et al. | |
| 7,341,758 B2 | 3/2008 | Stewart et al. | |
| 7,487,684 B2 | 2/2009 | Gupta et al. | |
| 7,507,312 B2 | 3/2009 | Bossi et al. | |
| 7,509,876 B1 | 3/2009 | Sokol et al. | |
| 7,707,873 B2 | 5/2010 | Degertekin | |
| 7,770,454 B2 | 8/2010 | Sokol et al. | |
| 7,900,516 B2 | 3/2011 | Fukutomi et al. | |
| 8,132,460 B1 | 3/2012 | Toller et al. | |
| 8,250,928 B2 * | 8/2012 | Miller | B29C 65/8284 73/779 |
| 8,359,924 B1 | 1/2013 | Bossi et al. | |
| 8,397,580 B2 * | 3/2013 | Georgeson | B29C 65/4855 73/760 |
| 8,511,165 B2 * | 8/2013 | Lopez Jauregui | G01N 29/043 381/338 |
| 8,527,218 B2 | 9/2013 | Georgeson et al. | |
| 8,616,068 B2 * | 12/2013 | Miller | B29C 65/8284 73/779 |
| 8,641,845 B2 * | 2/2014 | Bruck | B23K 1/19 156/272.4 |
| 8,714,016 B2 | 5/2014 | Stewart et al. | |
| 8,726,737 B2 * | 5/2014 | Georgeson | B29C 65/4855 73/760 |
| 8,785,814 B1 * | 7/2014 | Toller | B23K 26/16 219/121.72 |
| 2005/0120803 A1 * | 6/2005 | Sokol | G01N 29/2412 73/801 |
| 2010/0005896 A1 * | 1/2010 | Miller | B29C 65/8284 73/779 |
| 2011/0118994 A1 * | 5/2011 | Georgeson | G01N 29/2412 702/43 |
| 2012/0240681 A1 * | 9/2012 | Lopez Jauregui | G01N 29/043 73/643 |
| 2013/0081475 A1 * | 4/2013 | Miller | B29C 65/8284 73/779 |
| 2013/0147636 A1 * | 6/2013 | Georgeson | B29C 65/4855 340/870.02 |
| 2013/0192373 A1 * | 8/2013 | Stewart | G01N 29/2418 73/588 |
| 2015/0128709 A1 * | 5/2015 | Stewart | G01N 29/11 73/588 |

* cited by examiner

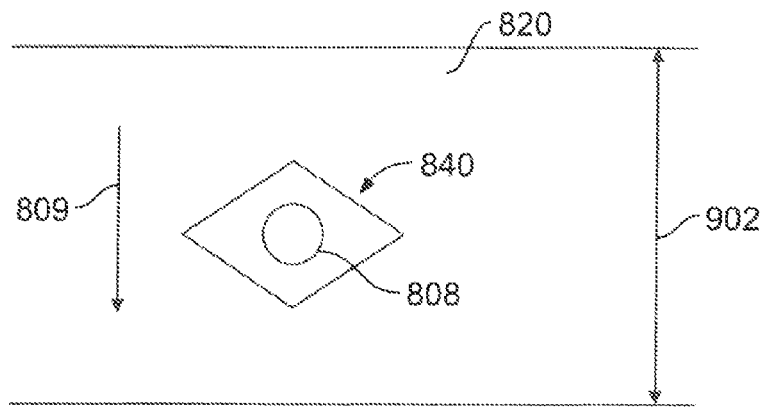
FIG. 9
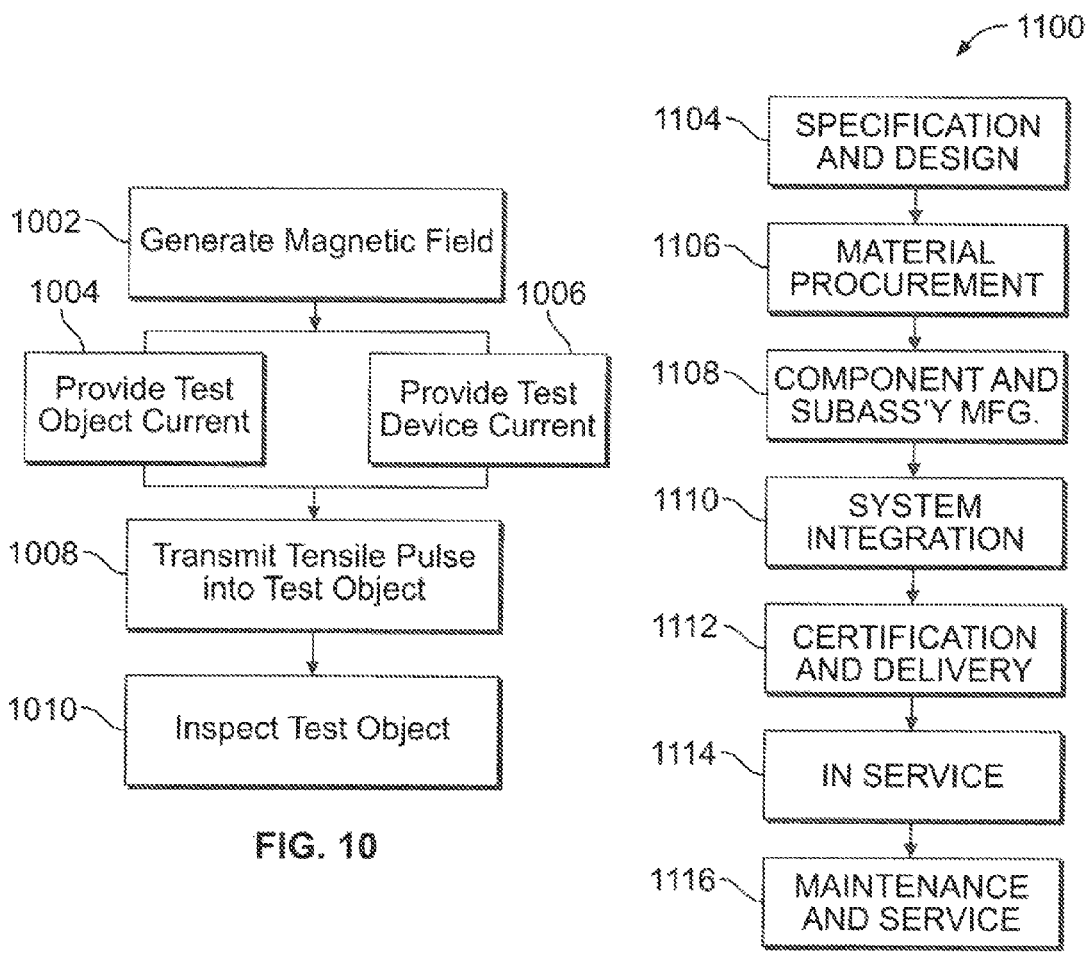
FIG. 10
FIG. 11

SYSTEMS AND METHODS FOR TESTING INTERNAL BONDS

FIELD OF EMBODIMENTS OF THE DISCLOSURE

Embodiments of the present disclosure generally relate to systems and methods for testing internal bonds of bonded structures.

BACKGROUND OF THE DISCLOSURE

Bonded structures (e.g., structures having a metallic layer bonded to a composite layer) may be utilized in a variety of applications, including aerospace. In some applications, the ability of the bond to withstand tension (or a force urging separation of the layers at the bond) may need to be tested. Certain approaches to testing bond strength require joining of a transducer assembly to a surface via an adhesive. Such use of adhesives may increase the time of testing, for example by requiring time to allow adhesive to set-up and/or time to break the adhesive bond and remove residual adhesive from a test object after testing.

SUMMARY OF THE DISCLOSURE

Accordingly, reduction of time and/or expense of evaluating bonded parts to verify that internal bonds meet strength requirements are provided in various embodiments disclosed herein.

Certain embodiments of the present disclosure provide a transducer assembly configured to test an internal bond of a test object having a metallic portion corresponding to a test surface to which the transducer assembly is configured to be coupled. The transducer assembly includes a magnetic portion, a body, a tensile pulse transmitter, and a pulse and current control unit. The magnetic portion includes at least one magnet and is configured to provide a magnetic field. The magnetic portion has an opening therein oriented toward the test surface. The body is disposed within the opening of the magnetic portion, and has a conductive portion configured to pass electric current near a body surface oriented toward the test surface. The body has a cavity therein oriented toward the test surface. The tensile pulse transmitter is disposed within the cavity of the body and configured to transmit a tensile pulse into the test object. The pulse and current control unit is configured to control the tensile pulse transmitted by the tensile pulse transmitter, and is configured to provide a current that passes through the conductive portion of the body and the test object, whereby a force urging the transducer assembly and the test object toward each other is generated responsive to the magnetic field and the current.

Certain embodiments of the present disclosure provide a method of testing an internal bond of a test object having a metallic portion corresponding to a test surface. The method includes coupling a transducer assembly to the test surface. The transducer assembly includes a magnetic portion, a body, a tensile pulse transmitter, and a pulse and current control unit. The magnetic portion includes at least one magnet and an opening therein oriented toward the test surface. The body is disposed within the opening of the magnetic portion, and has a conductive portion configured to pass electric current near a body surface oriented toward the test surface. The body has a cavity therein oriented toward the test surface. The tensile pulse transmitter is disposed within the cavity of the body and is configured to transmit a tensile pulse into the test object. The pulse and current control unit is configured to control the tensile pulse transmitted by the tensile pulse transmitter. The method also includes providing, via the magnetic portion, a magnetic field oriented along the test surface. Further, the method includes providing, via the pulse and current control unit, a current that passes through the conductive portion of the body and the test object, whereby a force urging the transducer assembly and the test object toward each other is generated responsive to the magnetic field and the current. Also, the method includes transmitting, via the tensile pulse transmitter, a tensile pulse into the test object.

Certain embodiments of the present disclosure provide a method of testing an internal bond of a test object having a metallic portion corresponding to a test surface. The method includes generating a magnetic field. The method also includes providing a test object current passing through the test object to generate, in cooperation with the magnetic field, a force urging a test device and the test object toward each other. Also, the method includes transmitting a tensile pulse into the test object to test the internal bond.

BRIEF DESCRIPTION OF THE DRAWINGS

FIG. 9 is a plan schematic view of the transducer assembly of FIG. 8.

FIG. 10 is a flowchart of a method, according to an embodiment of the present disclosure.

FIG. 11 is a block diagram of aircraft production and service methodology.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features.

Moreover, unless explicitly stated to the contrary, embodiments "comprising" or "having" an element or a plurality of elements having a particular property may include additional elements not having that property.

Embodiments of the present disclosure provide systems and methods for testing an internal bond of a bonded structure and/or providing a transducer assembly for testing an internal bond. In various embodiments, two metals (e.g., a metallic surface of a test object and a metallic surface of a transducer) are urged together temporarily at an interface to permit transmission of an ultrasound tension wave pulse to cross an interface into the test object without the use of adhesive to secure or join the transducer and test object. Compressive forces at the interface are generated over thin surface regions allowing a net tension pulse to exist once the pulse has traveled beyond the thin surface region of the test object. The tension pulse may be used to stress an internal bond between a metallic layer of the test object and another material of the test object, thereby providing a way of validating the required bond strengths within the bonded portions of the test object.

In various embodiments, electrical currents in the presence of a magnetic field are employed to generate pressure via a Lorentz force. The currents may be pulsed, resulting in the tendency of the currents to remain close to the surface, thereby generating the desired pressure only within the surface region. The contact region between a transducer and a test object may be relatively small (e.g., a circular area having a diameter of about 0.5 inches) to concentrate forces that are generated over a larger area. For example, a pressure of about 5000 pounds per square inch (psi) may be generated over the contact region in some embodiments. The tension wave may be transmitted to the test object through the contact area.

Embodiments of the present disclosure provide efficient evaluation of bond strengths in bonded parts without the use of adhesive to attach bond evaluation hardware (e.g., a transducer) to a bonded part being evaluated. Reduction of time and/or expense of evaluating bonded parts to verify that internal bonds meet strength requirements are accordingly provided.

Figure 1:
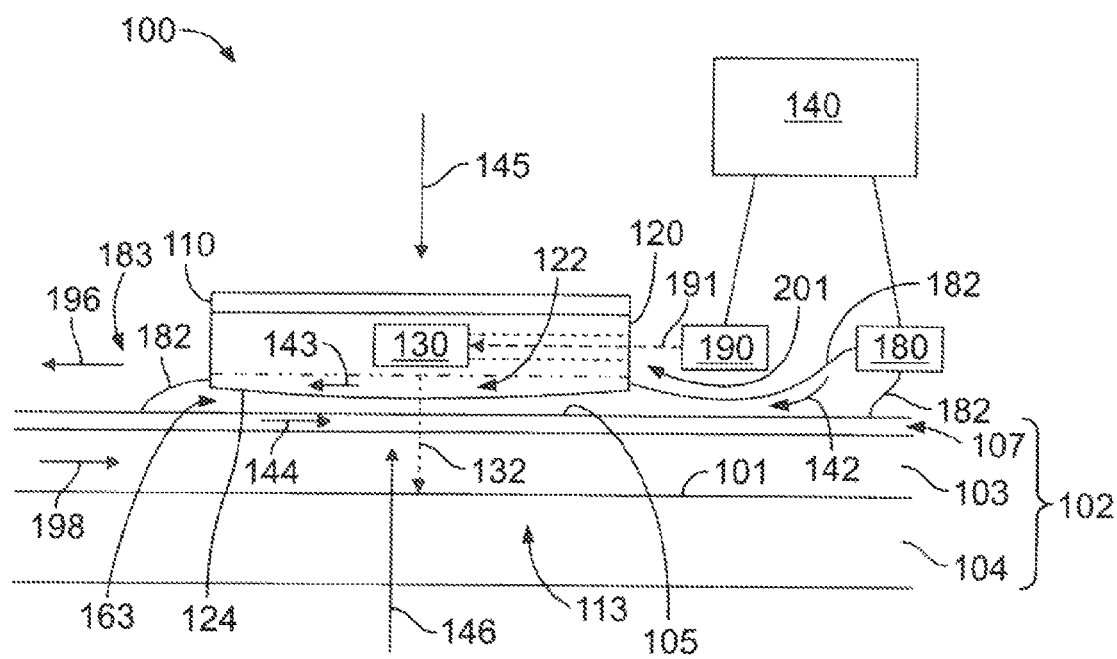
FIG. 1 illustrates a schematic side view diagram of a transducer assembly for testing an internal bond of a test object, according to an embodiment of the present disclosure.
Figure 2:
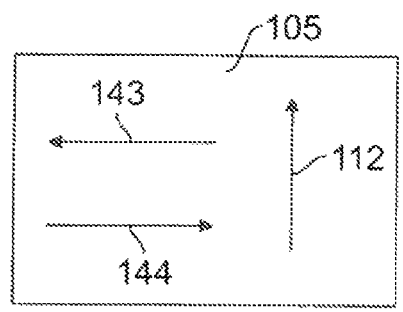
FIG. 2 is a diagrammatic plan view of magnetic field and electric current directions for the assembly of FIG. 1, according to an embodiment of the present disclosure.
Figure 3:
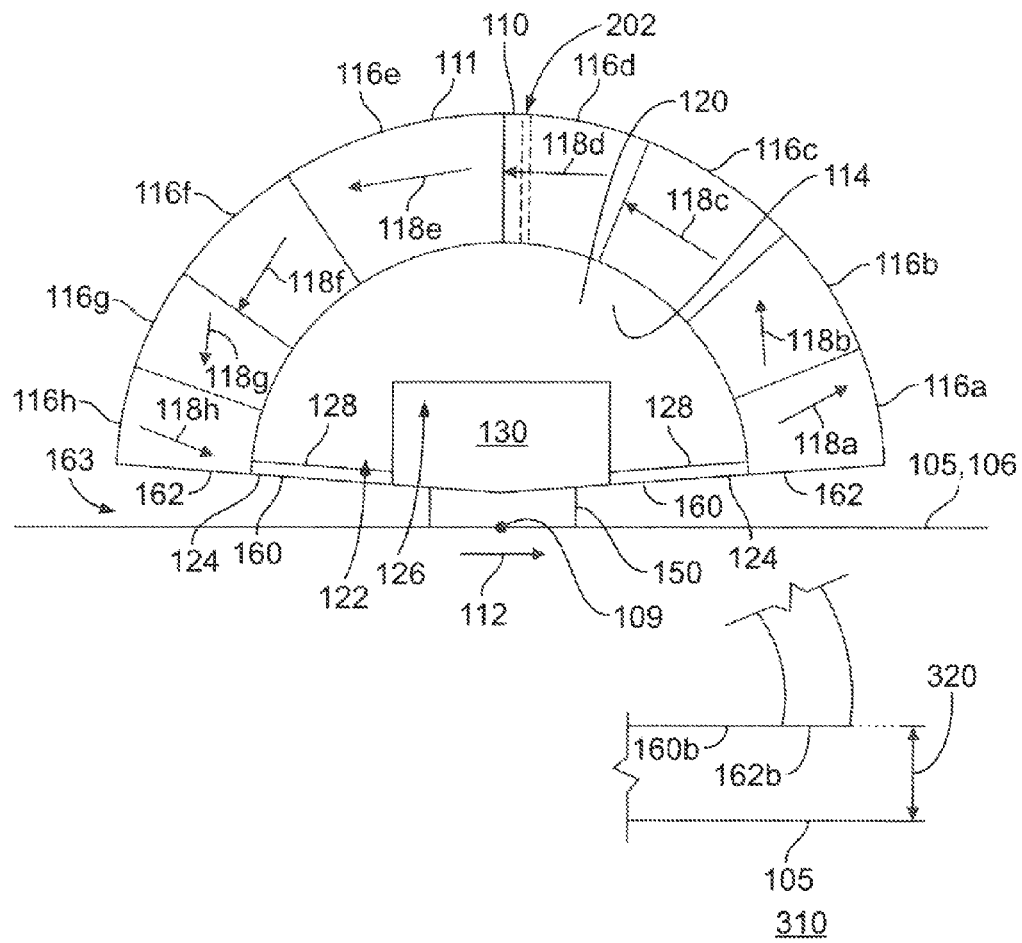
FIG. 3 is a schematic cross-sectional view of a transducer assembly, according to an embodiment of the present disclosure.

FIG. 1 illustrates a schematic block diagram of a transducer assembly 100 for testing an internal bond, according to an embodiment of the present disclosure. FIG. 2 provides a diagrammatic plan view of magnetic field and electric current directions for the assembly of FIG. 1, and FIG. 3 illustrates a schematic cross-sectional view of a transducer assembly. In the illustrated embodiment (as best seen in FIG. 1), the transducer assembly 100 is being used to test an internal bond 101 of a test object 102.

The test object 102, for example, may be a portion of a structure for an aerospace vehicle such as an airplane. The test object 102 may include layers having a common or similar surface area that are bonded together. In the illustrated embodiment, the test object 102 includes a first portion 103 and a second portion 104 joined by the bond 101. In the illustrated embodiment, the first portion 103 is a metallic portion. In some embodiments, the first portion 103 may be a metallic portion, the second portion 104 may be a carbon fiber portion or composite portion, and the bond 101 may be an adhesive or epoxy. In various embodiments, the test object 102, for example, may have a thickness between one millimeter and five centimeters. The transducer assembly 100 is configured to be coupled to a test surface 105, which in the illustrated embodiment is disposed on an external surface of the metallic portion 103 of the test object 102. In the illustrated embodiment, the test object 102 is shown as being formed of two portions joined along a bond. In various embodiments, more portions and bonds may be utilized in the test object 102. Generally, layer to layer bond strength may be tested in various embodiments.

As best seen in FIGS. 1 and 3, the transducer assembly 100 includes a magnetic portion 110, a body 120, a tensile pulse transmitter 130, and a pulse and current control unit 140. Generally, in the illustrated embodiment, the magnetic portion 110 provides a magnetic field 112. A current is passed through the body 120 in a first direction 196 and through the test object 102 (e.g., as discussed herein, through a narrow portion of the test object 102 disposed proximate to the transducer assembly 100) in a second direction 198 that is opposite to the first direction 196. The current 143 passing through the body 120, in conjunction with the magnetic field 112 provided by the magnetic portion 110, generates a resultant force 145 that urges the body 120 toward the test object 102. Similarly, the current 144 passing through the test object 102, in conjunction with the magnetic field 112 provided by the magnetic portion 110, generates a resultant force 146 that urges the test object 102 toward the body 120. The resultant forces 145, 146 cooperate to urge the transducer assembly 100 and test object 102 together, allowing the transducer assembly 100 to be used to test the internal bond 101 of the test object 102 (e.g., via of a tension or tensile pulse into the test object) without the use of adhesive to secure the transducer assembly 100 to the test object 102. It may be noted that the mechanical connection between the magnetic portion 110 and the body 120 may include an elastic material interposed between the magnetic portion 100 and the body 120, or utilize a spring or other mechanism to provide a sufficiently elastic mounting to permit the body 120 (or conductor mounted to the body 120) to move relative to the magnetic portion 110. Accordingly, during the duration of the current pulse, the body 120 may move sufficiently to generate an appropriate force. The inertia of the magnetic body 110 may act to maintain the magnetic body 110 substantially or essentially in place during the duration of a pulse.

In various embodiments, the magnetic portion 110 may include one or more permanent magnets 116a, 116b, 116c, 116d, 116e, 116f, 116g, 116h. In the illustrated embodiment, the magnetic portion 110 includes a plurality of permanent magnets 116a, 116b, 116c, 116d, 116e, 116f, 116g, 116h having individual magnetization directions 118a, 118b, 118c, 118d, 118e, 118f, 118g, 118h which provide fields that combine to form a magnetic field 112 at a region including a test point. In some embodiments, the magnetic portion 110 includes or defines an annular member 111 (e.g., a truncated ring), with individual permanent magnets 116a, 116b, 116c, 116d, 116e, 116f, 116g, 116h as segments of the annular member 111. The annular member 111 formed by the individual magnet segments 116 has a generally half-circle shape. It may be noted that the depicted magnetic portion 110 subtends an arc of slightly less than 180 degrees due to relieved surfaces 162 (the body 120 has corresponding relieved surfaces 160) discussed elsewhere herein. It may be noted that other configurations of relieved surfaces may be employed in various embodiments. For example, as seen in view 310, the relieved surfaces 160b and/or 162b may be parallel to the test surface 105 but offset by a predetermined distance 320 (e.g., the magnetic portion 110 may subtend an arc of 180 degrees and be offset by a constant distance from the test surface 105). In the illustrated embodiment, the test surface 105 corresponds to the diameter 106 defined by the magnetic portion 110 (e.g., the diameter 106 is at or near the test surface 105), and the magnetic field 112 is oriented along (e.g., parallel with) the diameter 106 or test surface 105. It may be noted that the magnetic field 112 may not be exactly parallel with the diameter 106 or test surface 105. Generally, the magnetic portion 110 will be more efficient in terms of strength of magnet required to produce a desired compressive force between the transducer assembly 100 and the test object 105 the closer the magnetic field 110 is to parallel with the test surface 105. The magnetic portion 110 defines an opening 114. For example, with the magnetic portion 110 defining a generally half-circularly shaped annular member 111, the opening 114 is disposed toward the center 109 of the half-circularly shaped annular member 111 and is generally half-cylindrically shaped.

In the illustrated embodiment, the body 120 is generally half-cylindrically shaped, and sized and configured to be disposed in the opening 114 of the magnetic portion 110. The body 120 includes a conductive portion 122 that is configured to facilitate the passage of an electrical current 143 near a body surface 124 oriented toward the test surface 105. Also, the body 120 includes a cavity 126 oriented toward the test surface 105. The cavity 126 is configured to accept the tensile pulse transmitter 130. In various embodiments, the body 120 may be formed entirely of an electrically conductive material, such as tungsten or other metal. In other embodiments, the body 120 may have one or more portions formed from a different material, and have a conductive material used to form the conductive portion 122 disposed near the body surface 124. It may be noted that, even if the entire body 124 is made of a conductive material, a pulsed current 143 of appropriate duration passing near the body surface 124 will tend to remain near the body surface 124, providing a relatively low inductance. The body 124 in various embodiments provides structural support to the tensile pulse transmitter 130 and/or the magnetic portion 110, and provides a pathway for a current 143 that may be used in conjunction with the magnetic field 112 to provide a compressive force 145 urging the transducer assembly 100 toward the test object 105.

The conductive portion 122 may define substantially all of the body 120, or a smaller proportion thereof. Generally, at least a portion of the conductive portion 122 is disposed at or near the body surface 124. For example, in some embodiments, an insulating member 128 (see FIG. 3) may be disposed on an external surface of the conductive portion 122 and interposed between the body 120 and the test surface 105. The insulating member 128 may be a relatively thin (e.g., 1 or 2 mil thick) electrically insulating film, and prevents or inhibits the transfer of current between the body 120 and the test object 102, helping to maintain distinct currents passing through the body 120 and the test object 102 during operation of the transducer assembly 100.

In the illustrated embodiment, as best seen in FIG. 1, a current 142 is provided to the body 120 of the transducer assembly 100. A first current portion 143 of the current 142 passes through the conductive portion 122 of the body 120 disposed near the body surface 124. A second current portion 144 of the current (or return portion) passes through the test object 102, with the second current portion 144 passing in a generally opposite direction to the first current portion 143. The first current portion 143, in conjunction with the magnetic field 112, generates a first resultant force 145 that urges the transducer assembly 100 toward the test object 105. The second current portion 144, in conjunction with the magnetic field 112, generates a second resultant force 146 that urges the test object 105 toward the transducer assembly 100. Because the current portions pass in generally opposite directions to each other, the resulting forces are generally oriented in opposite directions to each other as well.

It may further be noted that the current applied via the transducer assembly 100 tends to pass near the test surface 105 and thus passes through zones limited to surface areas, allowing penetration of a tensile pulse 132 into an interior region 113 of the test object 102 at which the internal bond 101 is located. For example, in the illustrated embodiment, the second current portion 144 passes through a current transmission zone 107 located near the test surface 105. As the current 144 is generally limited to the relatively narrow current transmission zone 107, the resulting compressive force 146 is also generally limited to the relatively narrow current transmission zone 107, thereby allowing a net tension pulse to exist in the interior region of the test object (e.g., proximate the internal bond 101) once the pulse 132 has traveled beyond the relatively narrow current transmission zone 107.

Generally, the compressive pressure provided by the forces 145, 146 must meet or exceed the tensile pressure to be transmitted to the internal bond 101. It may be noted that it may be difficult or impractical to provide sufficiently strong magnet fields and/or electrical currents to generate a desired test pressure over the entire surface of the transducer assembly 100 oriented toward the test surface 105. In the illustrated embodiment, the transducer assembly 100 includes a contact member 150 operably coupled (e.g., by a physical contact) to the tensile pulse transmitter 130, and interposed between the body 120 and the test surface 105. Generally, the contact member 150 is configured to contact the test surface 105, and to provide for focused application of the compressive forces 145, 146 urging the test object 102 and the transducer assembly 100 together to increase the compressive pressure, thereby increasing the magnitude of a tensile pulse 132 that may be transmitted through the current transmission zone 107 and into the interior of the test object 102 to the internal bond 101. The tensile pulse is also transmitted from the tensile pulse transmitter 130 to the test object 102 via the contact member 150. The contact member 150, for example, may be a relatively thin, disc-shaped member. The contact member 150, for example, may have a diameter of about 0.5 inches. The contact member 150 may be formed from a metallic material, and may be electrically insulated from the body 120 and/or the test object 102.

It may be noted that, as the current 143 passes through the body surface 124 of the body 120, the entire body 120 is drawn toward the test surface 105. However, if the body 120 contacts the test surface 105, the increase in pressure provided by use of the contact member 150 will be reduced or eliminated, depending on the surface area of the body 120 that contacts the test surface 150. As the forces 145, 146 increase and/or the length (or width) of the body 120 increases, it may become difficult or impractical to provide a body with sufficient rigidity to avoid contact with the test surface 105. Accordingly, the body 120 (and/or magnetic portion 110) may include relieved surfaces 160, 162 (e.g., surfaces having a negative camber, or sloped away from the test surface) to provide an increased range of deflection before contact with the test surface. In the illustrated embodiment, as best seen in FIGS. 1 and 3, the body 120 includes relieved surfaces 160 and the magnetic portion 110 includes relieved surfaces 162 spaced a variable distance 163 from the test surface 105.

The depicted tensile pulse transmitter 130 is disposed within the cavity 126 of the body 120, and is configured to transmit a tensile pulse 132 into the test object 102. The tensile pulse 132 is configured to penetrate into the test object 102 to subject the internal bond 101 to a tension urging the first portion 103 and the second portion 104 of the test object 102 away from each other. After the internal bond 101 has been subject to a desired magnitude and/or number of tensile pulses 132 in one or more locations of the test object 102, the test object 102 may be inspected to determine if the test object 102 has withstood the tension experienced by the internal bond 101. The tensile pulse 132 is configured to provide a test tension to determine if the internal bond 101 is sufficient for approval of use of the test object 102 in a particular application. The magnitude of the tensile pulse 132 may be determined based on the application for which the test object 102 is to be used. For a given application, a standardized or otherwise predetermined tension capability may be used to determine the magnitude or configuration of the tensile pulse 132.

In some embodiments, coherent light (e.g., from a laser) may be utilized to provide the tensile pulse 132. For example, as best seen in FIG. 1, in the depicted embodiment, a laser unit 190 may be controlled by the pulse and current control unit 140 to provide laser energy 191 to the tensile pulse transmitter 130, with the tensile pulse transmitter 130 generated the tensile pulse 132 responsive to reception of the laser energy 191. For additional details regarding generation of a tension wave or pulse using coherent light, see U.S. Pat. No. 8,714,016, issued May 6, 2014, entitled "Tension Wave Generation System," the entire subject matter of which is incorporated by reference herein.

Figure 4:
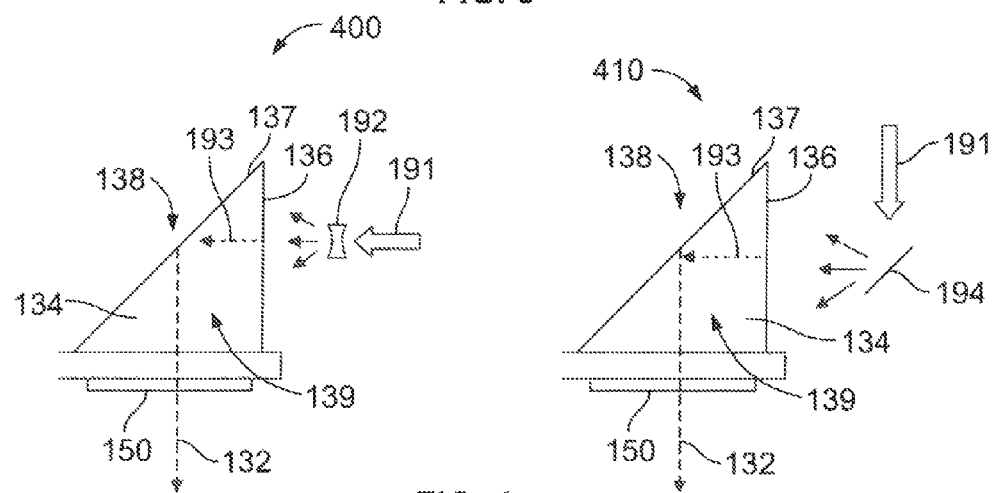
FIG. 4 illustrates side schematic views of example tensile pulse transmitters that utilize laser energy to generate a tensile pulse, according to embodiments of the present disclosure.

For example, the tensile pulse transmitter 130 may include a prism 134 (see FIG. 4) and an absorber surface 136 (see FIG. 4), with the pulse and current control unit 140 controlling the laser 190 to provide the laser energy 191 to the absorber surface 136. A compression pulse 193 (See FIG. 4) is generated within the tensile pulse transmitter 130 responsive to the laser energy 191 and converted to a tensile pulse 132 via the prism 134, with the tensile pulse 132 transmitted to the test object 102. In various embodiments, a hole or opening 201 running along the length of the body 120 (e.g., parallel to an axis of the semi-circle defined by the cross-section of the magnetic portion 110 and the body 120) from the laser unit 190 to the tensile pulse transmitter 130 may be utilized in conjunction with a lens 192 (see FIG. 4) to provide laser energy 191 (see FIG. 4) to the tensile pulse transmitter 130. As another example, a hole or opening 202 extending from a round surface of the annular member 111 radially inward toward the center 109 may be utilized in conjunction with a mirror 194 (see FIG. 4) to provide laser energy 191 to the tensile pulse unit 130. FIG. 4 illustrates side schematic views of example tensile pulse transmitters 400, 410 that utilize laser energy 191 to generate a tensile pulse 132. FIG. 4 illustrates an example tensile pulse transmitter 400 that utilizes a lens 192, and also an alternate example tensile pulse transmitter 410 that utilizes a mirror 194. The tensile pulse transmitter 400 utilizes a lens 192 to direct the laser energy 191 toward an absorber surface 136. The prism 134 includes a first portion 139 made of a transducer material, and a reflecting surface 137 separating the transducer material from an open portion 138. The open portion 138 may include air. When the laser energy 191 strikes the absorber surface 136, a compression pulse 193 is generated in the transducer material of the first portion 139 that travels toward the reflecting surface 137. At the reflecting surface 137, the tensile pulse 132 is generated responsive to the impingement of the compressive pulse on the reflecting surface 137, with the tensile pulse 132 directed toward the test surface 105 via the contact member 150.

As also seen in FIG. 4, the tensile pulse transmitter 410 utilizes a mirror 194 to direct the laser energy 191 toward an absorber surface 136. Similarly, the prism 134 of the tensile pulse transmitter 410 includes a first portion 139 made of a transducer material, and a reflecting surface 137 separating the transducer material from an open portion 138. The open portion 138 may include air. When the laser energy 191 directed by the mirror 194 strikes the absorber surface 136, a compression pulse 193 is generated in the transducer material of the first portion 139 that travels toward the reflecting surface 137. At the reflecting surface 137, the tensile pulse 132 is generated responsive to the impingement of the compressive pulse 193 on the reflecting surface 137, with the tensile pulse 132 directed toward the test surface 105 via the contact member 150.

With continued reference to FIG. 1, the pulse and current control unit 140 is configured to control the tensile pulse 132 transmitted by the tensile pulse transmitter 130. The pulse and current control unit 140 is also configured to provide the current 142 that passes through the conductive portion 122 of the body 120 and the test object 102. As discussed herein, the passage of the current through the body 120 and current through the test object 102, in conjunction with the magnetic field 112, generate forces urging the transducer assembly 100 and the test object 102 toward each other. Accordingly, the use of adhesive to join the transducer assembly 100 and the test object 102 is avoided. Generally, in various embodiments, the pulse and current control unit 140 includes processing circuitry and a tangible, non-transitory memory, and is configured (e.g., programmed) to provide a desired current 142 for urging the transducer assembly 100 and test object 102 together, as well as energy (e.g., laser energy) to provide a desired tensile pulse 132 via the tensile pulse transmitter 130. The particular current 142 and/or tensile pulse 132 may be selected based on the test application. The amplitude and duration of a current pulse 142, for example, may be selected to provide sufficient compressive forces 145, 146 between the test object 102 and the transducer assembly 100, and to have a duration such that the current 144 resides entirely or predominantly within a relatively thin zone 107 near the surface of the test object 102.

In the illustrated embodiment, the pulse and current control unit 140 is operably coupled to a power supply 180 and provides control signals to control the operation of the power supply 180 to provide the current 142. As seen in FIG. 1, the depicted power supply 180 is coupled to transducer assembly 100 and test object 102 via conductive pathways or links 182 to define a circuit 183 connecting the power supply 180, body 120 (e.g., conductive portion 122 of the body 120), and test object 102 in series, and to provide a current 143, 144 passing near opposed surfaces of the body 120 of the transducer assembly 100 and the test object 102. The current 142, 143, 144 may be provided as a pulse. For example, the power supply 180 may include a critically damped RLC (resistor, inductor, capacitor) circuit to provide a pulsed current 142 to the transducer assembly 100 and the test object 102. The pulsed current 142 may be controlled to provide a current having an amplitude that varies between a magnitude of zero and a maximum positive amplitude. In the illustrated embodiment, the pulsed current 142 may be controlled to avoid any negative values, as such negative values would result in forces that urge the transducer assembly 100 and test object 102 away from each other. The depicted pulse and current control unit 140 also controls the laser unit 190 to provide the laser energy 191 to the tensile pulse transmitter 130. The laser energy 191 may also be provided to the tensile pulse transmitter 130 intermittently, or as a pulse.

Figure 5:
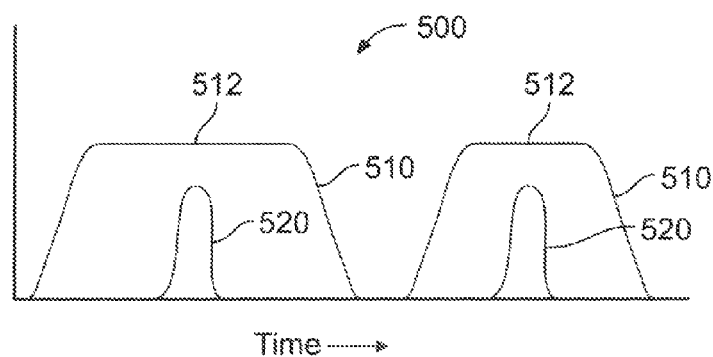
FIG. 5 illustrates a graph depicting current and laser pulses plotted against time, according to an embodiment of the present disclosure.

In various embodiments, the pulse and current control unit 140 may advantageously coordinate the timing of the laser energy pulse with the timing of the current pulse. For example, the tensile pulse (generated responsive to the laser pulse) may be provided proximate to a peak of the current pulse. FIG. 5 illustrates a graph 500 depicting current and laser pulses plotted against time. It may be noted that the particular configuration of the graph 500 depicted in FIG. 5 is provided by way of example for ease and clarity of illustration, and that other configurations of pulses (e.g., different durations of pulses, time intervals between pulses, magnitudes of pulses, or shapes of the pulses, among others) may be employed in various embodiments. As seen in FIG. 5, the current pulse 510 includes a peak 512. With reference to FIG. 1, because the current 143, 144 passes in relatively narrow zones 122, 107 near the surfaces of the body 120 and the test object 102, the area (and volume) through which the current 143, 144 passes may be relatively small, providing a relatively low inductance. The relatively low inductance allows for relatively quick activation and deactivation of the current pulse 510. The tensile pulse 520 (which corresponds to the laser pulse) is provided in the illustrated embodiment at or near a peak value of the current pulse 510, thereby allowing for the largest (or near largest) possible transmission of the tensile pulse through the zone of the test object 102 upon which the compressive force due to the interaction of the current pulse and the magnetic field acts, and into the interior of the test object 102 toward the internal bond 101.

Figure 6:
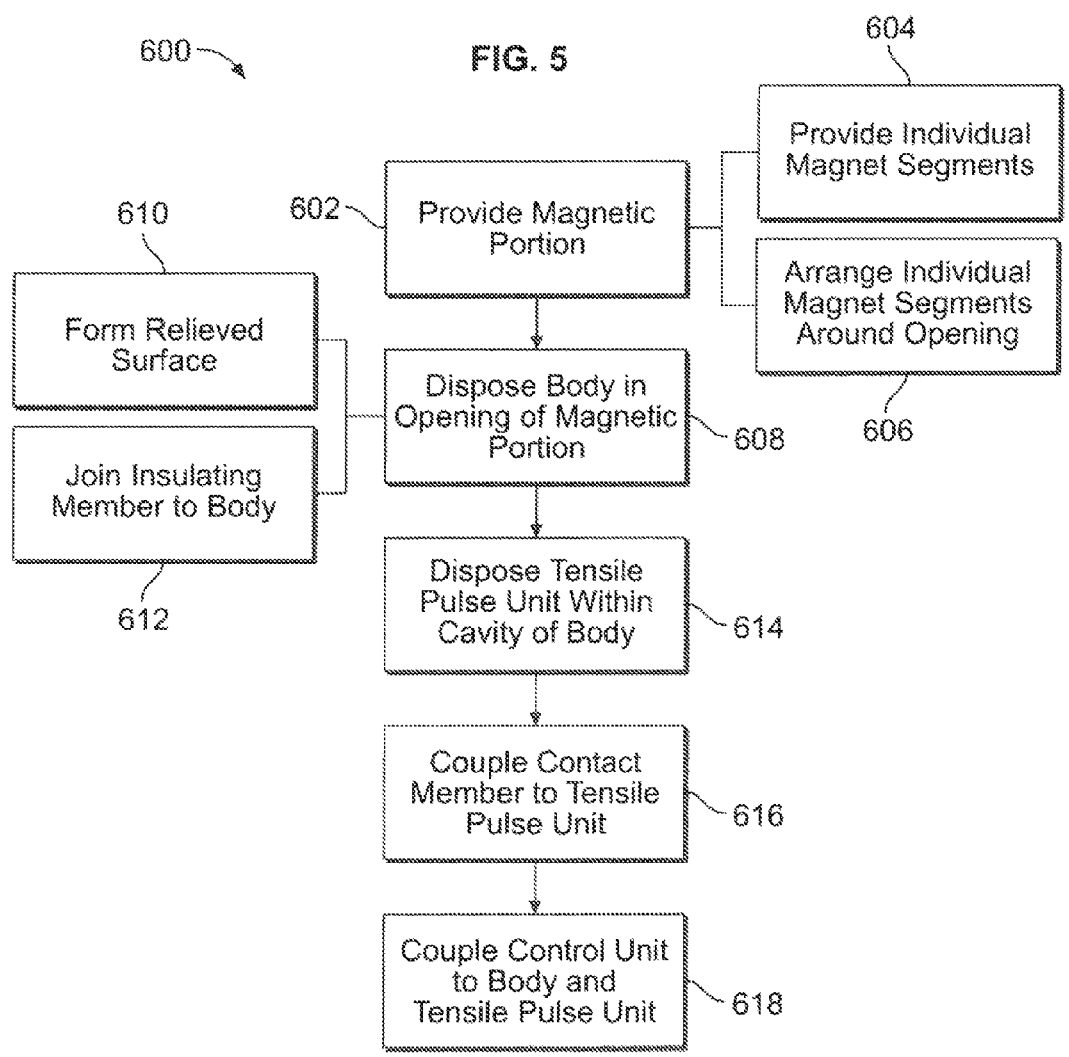
FIG. 6 is a flowchart of a method, according to an embodiment of the present disclosure.

FIG. 6 provides a flowchart of a method 600 for providing a transducer assembly, in accordance with various embodiments. The method 600, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion.

At 602, a magnetic portion (e.g., magnetic portion 110) is provided. The magnetic portion may include at least one magnet (e.g., a permanent magnet), and be configured to provide a magnetic field oriented along a test surface of an object having an internal bond to be tested. The magnetic portion in various embodiments includes an opening oriented toward the test surface. In some embodiments, the magnetic portion may be made of individual magnetic segments. For example, in the illustrated embodiment, at 604, individual magnetic segments are provided, and at 606, the individual magnetic segments are arranged around the opening. The magnetic segments may be formed of annular pie-shaped pieces that together form a magnetic portion having a generally half-circular cross-section. The magnetic segments may be configured such that the individual fields of the magnetic segments cooperate or combined to provide a net magnetic field having a desired orientation (e.g., an orientation that, in conjunction with currents provided through the transducer assembly and test object will result in compressive forces urging the transducer assembly and test object toward each other).

At 608, a body (e.g., body 120) is disposed (e.g., positioned and mounted) within the opening of the magnetic portion. As discussed herein, the body includes a conductive portion configured to pass electric current near a body surface oriented toward the test surface. The body also includes a cavity oriented toward the test surface. In the illustrated embodiment, at 610, a relieved surface is formed on the body and configured to reduce the risk of contact between the body and the test surface under the influence of the compressive forces generated by the interaction between the current passing through the body and the magnetic field provided by the magnetic portion. At 612, an insulating member (e.g., a thin electrically insulating film) is adhered, mounted, or otherwise joined to an external surface of the body, with the insulating member interposed between the body and the test surface. The insulating member provides electrical insulation between the body and the test object, thereby helping maintain differently oriented currents in the body and the test object and differently oriented resulting forces.

At 614, a tensile pulse transmitter (e.g., tensile pulse transmitter 130) is disposed (e.g., positioned and mounted) within the cavity of the body. The tensile pulse transmitter is configured to transmit a tensile pulse into the test object. For example, the tensile pulse transmitter may include a prism having a reflective surface configured to generate tensile pulses in response to a compression pulse passing through the tensile pulse transmitter to the reflective surface, with the compression pulse generated in response to the impingement of coherent light on an absorber surface of the tensile pulse transmitter.

At 616, a contact member (e.g., contact member 150) is coupled to the tensile pulse transmitter. The contact member is interposed between the body and the test surface. The contact member may be used to minimize a force application area or increase a compressive pressure resulting from the compressive forces urging the transducer assembly and test object toward each other.

At 618, a pulse and current control unit (e.g., pulse and current control unit 140) is operably coupled to the body and tensile pulse transmitter. As discussed herein, the pulse and current control unit is configured to control the tensile pulse transmitted by the tensile pulse transmitter, and configured to provide a current that passes through the conductive portion of the body and the test object.

Figure 7:
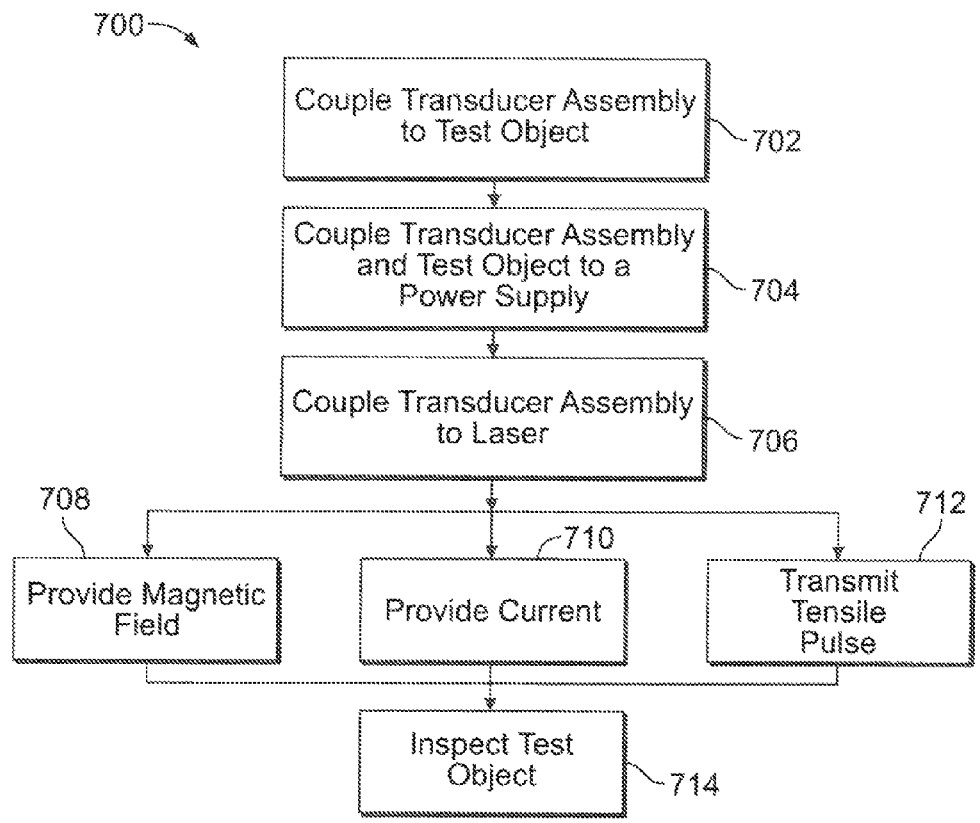
FIG. 7 is a flowchart of a method, according to an embodiment of the present disclosure.

FIG. 7 provides a flowchart of a method 700 for testing an internal bond, in accordance with various embodiments. The method 700, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the pulse and current control unit 140) to perform one or more operations described herein.

At 702, a transducer assembly (e.g., transducer assembly 100) is coupled to a test object (e.g., test object 102) having a metallic portion corresponding to a test surface (e.g., a test surface disposed on an exterior of the metallic portion). For example, the transducer assembly may be held by a robotic arm or other structure against or near a portion of the test object to be tested. It may be noted that the particular construction or configuration of the transducer assembly may correspond to an intended orientation. For example, a first configuration of a transducer assembly may be utilized in applications where the transducer assembly is maintained generally horizontal (e.g., oriented parallel to the horizon) with respect to a test object, and a second configuration utilized in applications where the transducer assembly is maintained generally vertical (e.g., oriented perpendicular to the horizon) with respect to a test object.

At 704, the transducer assembly and test object are coupled to a power supply (e.g., power supply 180). For example, a pulse and current control unit (e.g., pulse and current control unit 140) of the transducer assembly may be operably coupled to the power supply to control operation of the power supply, and the power supply electrically coupled to the body of the transducer assembly and to the test object, wherein electrical current may be passed through opposed surfaces of the body and test object.

At 706, the pulse and current control unit of the transducer assembly is coupled to a laser (e.g., laser unit 190). The laser unit may be aligned with a tensile pulse transmitter (e.g., tensile pulse transmitter 130) of the transducer assembly to provide coherent light to the tensile pulse transmitter which will be utilized by the tensile pulse transmitter to generate a tensile pulse.

At 708, a magnetic field is provided. For example, the transducer assembly may include a permanent magnet (e.g., magnetic portion 110) that provides a magnetic field oriented generally along the test surface. The magnetic field is configured to be oriented such that the magnetic field will generate compressive forces urging the transducer assembly toward the test object in cooperation with the current passing through the body of the transducer assembly and the test object.

At 710, a current is provided. In the illustrated embodiment, the current passes through a conductive portion of the body and through the test object. Compressive forces urging the transducer assembly and the test object toward each other are generated responsive to the magnetic field and the current. The current may be provided having a current pulse configured to maintain current within zones proximate exterior surfaces of the body of the transducer assembly and the test object.

At 712, a tensile pulse is transmitted, via the tensile pulse transmitter, into the test object. With the compressive forces generally limited to a zone near the surface of the test object, the tensile pulse may penetrate into the interior of the test object to subject an internal bond of the test object (located outside of the zone where the compressive forces act) to a desired tension for testing the integrity of the internal bond. For example, the pulse and current control unit may control a laser to provide energy to the tensile pulse transmitter at a desired time or interval. For example, the tensile pulse may be provided via triggering of a laser to provide a tensile pulse that occurs proximate (e.g., at or near) a peak of a current pulse passing through the test object and the body of the transducer assembly. In some embodiments, the tensile pulse may be transmitted to the test object via a contact member (e.g., contact member 150).

At 714, after administration of a desired amplitude and/or number of tensile pulses, the test object is inspected. If the internal bond is found to have withstood the administered tensile pulses, the test object may be considered as approved or having passed or satisfied the test. If the internal bond is found to have not withstood the administered tensile pulses, the test object may be considered as not approved or as having failed or not satisfied the test.

Figure 8:
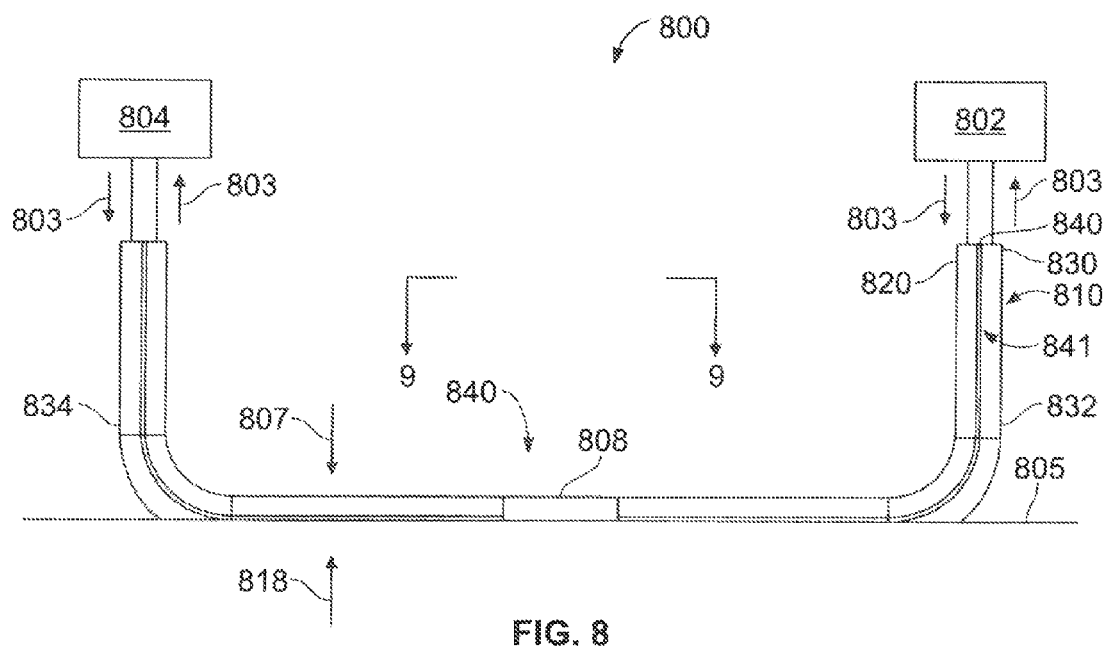
FIG. 8 is a side schematic view of a transducer assembly, according to an embodiment of the present disclosure.

As discussed herein, current may be passed through both a transducer assembly and a test object to generate forces cooperating to urge the transducer assembly and test object toward each other. For example, FIG. 8 is a side schematic view of a transducer assembly 800 showing various aspects used to direct a current through both the transducer assembly 800 and a test object 805, according to an embodiment of the present disclosure. FIG. 9 is a plan view taken along lines 9-9 shown in FIG. 8 of aspects of the transducer assembly 800.

As best seen in FIG. 8, the transducer assembly 800 includes a contact member 808 (which may be configured similarly to contact member 150) and a stripline 810. The stripline 810 is utilized to route current through the transducer assembly 800 and the test object 805. The stripline 810 may be mounted to a body of a transducer assembly (e.g., body 120). The depicted stripline 810 includes a first conductive path 820 and a second conductive path 830 with a dielectric member 840 interposed therebetween. The first conductive path 820, for example, may form all or a part of a conductive portion of a body to which the stripline 810 is mounted. The stripline 810 and/or a mounting arrangement coupling the stripline 810 to the transducer assembly 800 may be configured to be sufficiently flexible to allow for relative movement between the transducer assembly 800 (e.g., a body of the transducer assembly) and the test object 805. The first conductive path 820 and the second conductive path 830 may be formed, for example, from relatively thin, wide strips of a conductive material (e.g., a metal such as copper). For example, the stripline 810 may have a width 902 of one inch (about 2.5 centimeters) in various embodiments. In the illustrated embodiment, a current 803 flows from a current source 802, through the first conductive path 820 to an impedance-matched load 804. The current 803 then flows from the impedance-matched load 804 to the current source 802 via the second conductive path 830 and the test object 805 (e.g., an upper portion of the test object 805 or portion of the test object 805 nearest the transducer assembly 800). With the first conductive path 820 mechanically coupled to a body of the transducer (e.g., body 120), a current 803 passing through the first conductive path 820 in the presence of an appropriately oriented magnetic field 809 produces a force 807 urging the transducer assembly 800 toward the test object 805. Similarly, the current 803 passing through the test object 805 in the presence of the appropriately oriented magnetic field 809 produces a force 818 urging the test object 805 toward the transducer assembly 800. The impedance-matched load 804, for example, may be a resistor, such as a 50Ω resistor.

As seen in FIGS. 8 and 9, the first conductive path 820 includes an opening 840 that extends around the contact member 808. Accordingly, the contact member 808, which contacts the test object 805, may be electrically isolated from the first conductive path 820 either through a dielectric zone 841 between the contact member 808 and the first conductive path 820. The opening 840 also allows for the contact member 808 to translate independent of the stripline 810, allowing the forces 807, 808 urging the transducer assembly 800 and test object 805 together to be concentrated as discussed herein. The width 902 of the first conductive path 820 (as well as the width of the second conductive path 830), along with the size (e.g., length and width) of the opening 840 and the shape (e.g., taper of opening from narrowest to widest point) may be selected to provide a geometry corresponding to a desired impedance. Further, in various embodiments, the opening 840 may be sized to allow for insertion of a tensile pulse transmitter (e.g., tensile pulse transmitter 130) into a body (e.g., body 120) and removal of the tensile pulse transmitter 130 from the body 120 (e.g., upon exhaustion of an absorber material), allowing for replacement of the tensile pulse transmitter.

The second conductive path 830 includes a first portion 832 extending between the current source 810 and the test object 805, and a second portion 834 extending between the impedance-matched load 804 and the test object 805. The ends of the first portion 832 and the second portion 834 are maintained in contact with the test object 805, for example as a result of a force applied to hold the transducer assembly 800 against the test object 805. Thus, current (e.g., a return current) is allowed to flow from the impedance-matched load 804 to the test object 805 via the second portion 834 of the second conductive path 830, through the test object 805 from the second portion 834 to the first portion 832 of the second conductive path 830 via the test object 805, and to the current source 802 via the first portion 832 of the second conductive path 830.

FIG. 10 provides a flowchart of a method 1000 for testing an internal bond, in accordance with various embodiments. The method 1000 may be used to test an internal bond of a test object having a metallic portion that corresponds to a test surface, with the test surface oriented toward a transducer or other test device used to test the internal bond. The method 1000, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1000 may be able to be used as one or more algorithms to direct hardware (e.g., one or more aspects of the pulse and current control unit 140) to perform one or more operations described herein.

At 1002, a magnetic field is generated. The magnetic field may be oriented along the test surface, for example in a direction generally perpendicular to currents that will be passed through the transducer and test object near the test surface.

At 1004, a test object current is provided. The test object current is passed through the test object. The test object current, in cooperation with the magnetic field, generates a force urging the test device and the test object toward each other (e.g., by generating a force urging the test object toward the test device). In some embodiments, the test object current passes in a direction along the test surface generally perpendicular to the magnetic field. The test object current may be passed proximate to the test surface.

At 1006, a test device current is provided. The test device current is provided through a conductive portion of the test device. The test device current in the illustrated embodiment is passed in a direction opposite to the direction of the test object current. The test device current, in cooperation with the magnetic field, generates a force urging the test device and the test object toward each other (e.g., by generating a force urging the test device toward the test object). With the test object current and the test device current passed in opposite directions, the resulting forces will be oriented in opposite directions.

At 1008, a tensile pulse is transmitted into the test object to test the internal bond. The tensile pulse may be transmitted into the test object from the test device. The current passing through the test object may be generally limited to a zone proximate the test surface and away from the test bond so that any effect of the forces generated by the interaction of the magnetic field and the current on the tensile pulse at the internal bond to be tested is reduced or eliminated.

At 1010, after administration of a desired amplitude and/or number of tensile pulses, the test object is inspected. If the internal bond is found to have withstood the administered tensile pulses, the test object may be considered as approved or having passed or satisfied the test. If the internal bond is found to have not withstood the administered tensile pulses, the test object may be considered as not approved or as having failed or not satisfied the test.

Figure 12:
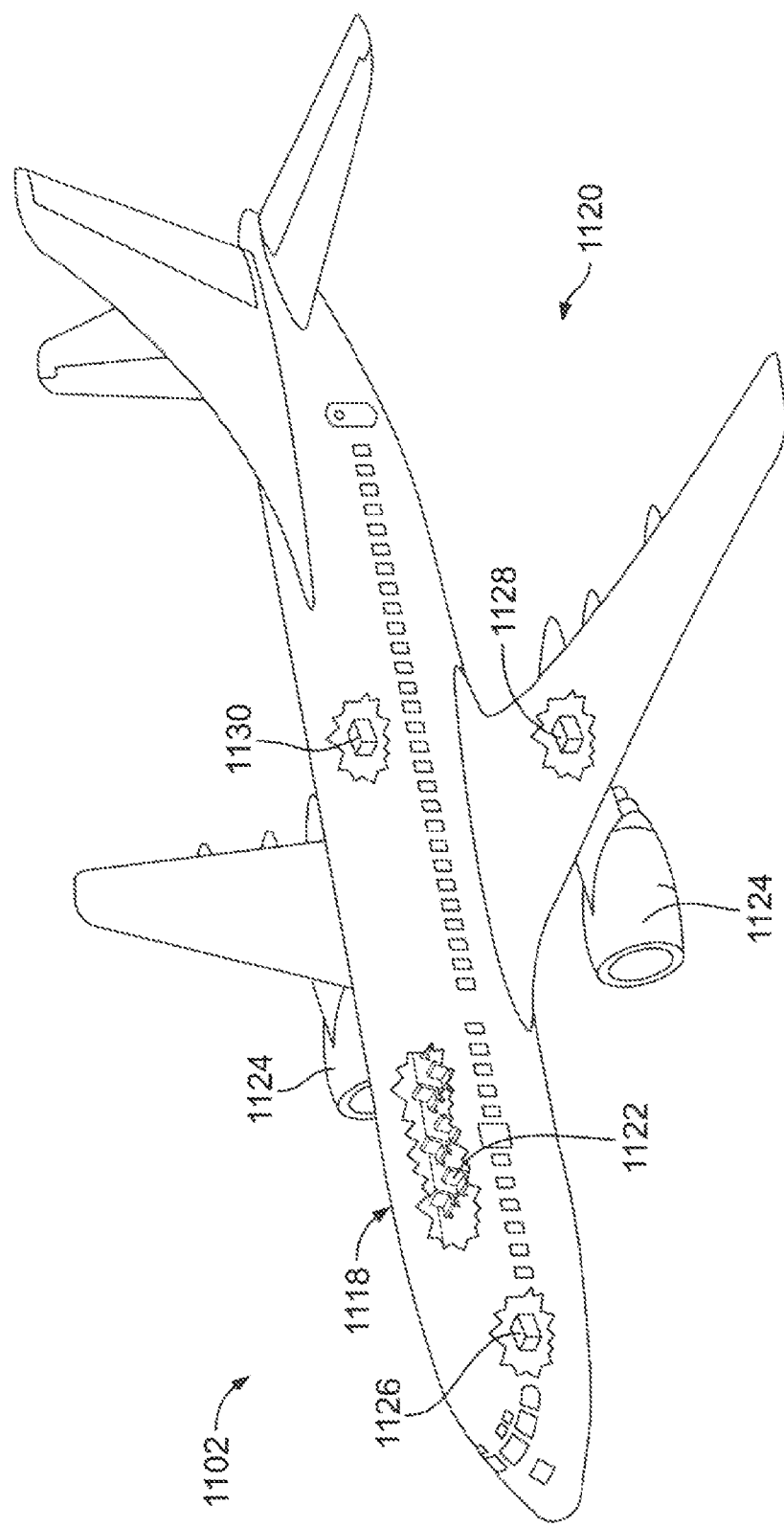
FIG. 12 is a schematic illustration of an aircraft.

Examples of the present disclosure may be described in the context of aircraft manufacturing and service method 1100 as shown in FIG. 11 and aircraft 1102 as shown in FIG. 12. During pre-production, illustrative method 1100 may include specification and design (block 1104) of aircraft 1102 and material procurement (block 1106). During production, component and subassembly manufacturing (block 1108) and system integration (block 1110) of aircraft 1102 may take place. Thereafter, aircraft 1102 may go through certification and delivery (block 1112) to be placed in service (block 1114). While in service, aircraft 1102 may be scheduled for routine maintenance and service (block 1116). Routine maintenance and service may include modification, reconfiguration, refurbishment, etc. of one or more systems of aircraft 1102. For example, in various embodiments, examples of the present disclosure may be used in conjunction with one or more of blocks 1108, 1110, 1112, or 1116.

Each of the processes of illustrative method 1100 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 12, aircraft 1102 produced by illustrative method 1100 may include airframe 1118 with a plurality of high-level systems 1120 and interior 1122. Examples of high-level systems 1120 include one or more of propulsion system 1124, electrical system 1126, hydraulic system 1128, and environmental system 1130. Any number of other systems may be included. Although an aerospace example is shown, the principles disclosed herein may be applied to other industries, such as the automotive industry. Accordingly, in addition to aircraft 1102, the principles disclosed herein may apply to other vehicles, e.g., land vehicles, marine vehicles, space vehicles, etc. In various embodiments, examples of the present disclosure may be used in conjunction with one or more of airframe 1118 or interior 1122.

Apparatus(es) and method(s) shown or described herein may be employed during any one or more of the stages of the manufacturing and service method 1100. For example, components or subassemblies corresponding to component and subassembly manufacturing 1108 may be fabricated or manufactured in a manner similar to components or subassemblies produced while aircraft 1102 is in service. Also, one or more examples of the apparatus(es), method(s), or combination thereof may be utilized during production stages 1108 and 1110, for example, by substantially expediting assembly of or reducing the cost of aircraft 1102. Similarly, one or more examples of the apparatus or method realizations, or a combination thereof, may be utilized, for example and without limitation, while aircraft 1102 is in service, e.g., maintenance and service stage (block 1116).

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus(es) and method(s) disclosed herein in any combination, and all of such possibilities are intended to be within the spirit and scope of the present disclosure.

Referring to FIGS. 1-12, embodiments of the present disclosure provide for testing of internal bonds of bonded structures without requiring the use of adhesives to secure the bonded structure to a transducer assembly. The time and cost of testing of bonded structures is reduced in various embodiments.

As used herein, the term "central processing unit," "CPU," "computer," "control unit," "module," or the like may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "central processing unit," "CPU," "computer," "control unit," or "module."

The computer or processor executes a set of instructions that are stored in one or more storage elements (such as one or more memories), in order to process data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The diagrams of embodiments herein may illustrate one or more control units or modules. It is to be understood that the control units or modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the modules may represent processing circuitry such as one or more of a field programmable gate array (FPGA), application specific integrated circuit (ASIC), microprocessor(s), a quantum computing device, and/or the like. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A transducer assembly configured to test an internal bond of a test object having a metallic portion corresponding to a test surface to which the transducer assembly is configured to be coupled, the transducer assembly comprising:
   a magnetic portion comprising at least one magnet and configured to provide a magnetic field, the magnetic portion having an opening therein oriented toward the test surface;
   a power supply configured to provide an electric current that passes through the transducer assembly and the test object;
   links configured to couple the power supply to the transducer assembly and the test object;
   a body having a conductive portion disposed within the opening of the magnetic portion, the conductive portion configured to pass the electric current from the power supply in a first direction near a body surface, the body surface oriented toward the test surface;
   a tensile pulse transmitter configured to transmit a tensile pulse into the test object; and
   a pulse and current control unit coupled to the conductive portion, the power supply, and the tensile pulse transmitter, the pulse and current control unit configured to control the power supply to provide the electric current through the conductive portion of the body in the first direction and through the test object in a second direction that is opposite to the first direction, whereby a force urging the transducer assembly and the test object toward each other is generated responsive to the magnetic field and the electric current.

2. The transducer assembly of claim 1, wherein the magnetic portion is configured to provide the magnetic field oriented along the test surface.

3. The transducer assembly of claim 1, wherein the body has a cavity therein oriented toward the test surface.

4. The transducer assembly of claim 3 wherein the tensile pulse transmitter is disposed within the cavity of the body.

5. The transducer assembly of claim 1, further comprising a contact member coupled to the tensile pulse transmitter and interposed between the body and the test surface.

6. The transducer assembly of claim 5, wherein at least one of the body or the magnetic portion have a relieved surface spaced a distance from the test surface.

7. The transducer assembly of claim 1, wherein the body comprises an insulating member interposed between the body and the test surface.

8. The transducer assembly of claim 1, wherein the pulse and current control unit is configured to provide the current having a current pulse, wherein the pulse and current control unit is further configured to provide the tensile pulse proximate to a peak of the current pulse.

9. The transducer assembly of claim 1, wherein the tensile pulse transmitter comprises a prism and an absorber surface, the pulse and current control unit controls a laser to provide laser energy to the absorber surface, a compression pulse is generated in the tensile pulse transmitter responsive to the laser energy, and the tensile pulse is transmitted toward the test surface via the prism.

10. The transducer assembly of claim 1, wherein the magnetic portion comprises a plurality of permanent magnets having individual fields that are combined to provide the magnetic field.

11. The transducer assembly of claim 10, wherein the magnetic portion defines an annular member, and the permanent magnets are configured as segments of the annular member.

12. A method of testing an internal bond of a test object having a metallic portion corresponding to a test surface, the method comprising:
   coupling a transducer assembly to the test surface, the transducer assembly comprising:
      a magnetic portion comprising at least one magnet and an opening therein oriented toward the test surface;
      a power supply configured to provide an electric current that passes through the transducer assembly and the test object;
      links configured to couple the power supply to the transducer assembly and the test object;
      a body disposed within the opening of the magnetic portion, the body having a conductive portion configured to pass the electric current from the power supply near a body surface oriented toward the test surface, the body having a cavity therein oriented toward the test surface;
      a tensile pulse transmitter disposed within the cavity of the body and configured to transmit a tensile pulse into the test object; and
      a pulse and current control unit configured to control the tensile pulse transmitted by the tensile pulse transmitter;
   providing, via the magnetic portion, a magnetic field oriented along the test surface;
   providing, via the power supply under control of the pulse and current control unit, the electric current through the conductive portion of the body in a first direction and through the test object in a second direction that is opposite the first direction, whereby a force urging the transducer assembly and the test object toward each other is generated responsive to the magnetic field and the current; and
   transmitting, via the tensile pulse transmitter, a tensile pulse into the test object.

13. The method of claim 12, wherein the tensile pulse is transmitted via a contact member operably coupled to the tensile pulse transmitter and interposed between the body and the test surface.

14. The method of claim 12, wherein the pulse and current control unit is configured to provide the current having a current pulse, wherein the tensile pulse is provided proximate to a peak of the current pulse.

15. The method of claim 12, wherein the tensile pulse transmitter comprises a prism and an absorber surface, and wherein providing the tensile pulse comprises providing laser energy to the absorber surface, wherein a compression pulse is generated in the tensile pulse transmitter and the tensile pulse is transmitted toward the test surface via the prism.

16. The method of claim 12, wherein the magnetic portion comprises a plurality of permanent magnets providing individual fields that are combined to provide the magnetic field.

17. A method of testing an internal bond of a test object having a metallic portion corresponding to a test surface, the method comprising:
   generating a magnetic field;
   providing, via a power supply coupled via links to a test device and the test object, an electric current that is passed through a test device in a first direction and passed through the test object in a second direction that is opposite to the first direction to generate, in cooperation with the magnetic field, a force urging the test device and the test object toward each other; and transmitting a tensile pulse into the test object to test the internal bond.

18. The method of claim 17, wherein the magnetic field is oriented along the test surface.

19. The method of claim 17, wherein the electric current is passed proximate to the test surface.

* * * * *